Figure 1B:
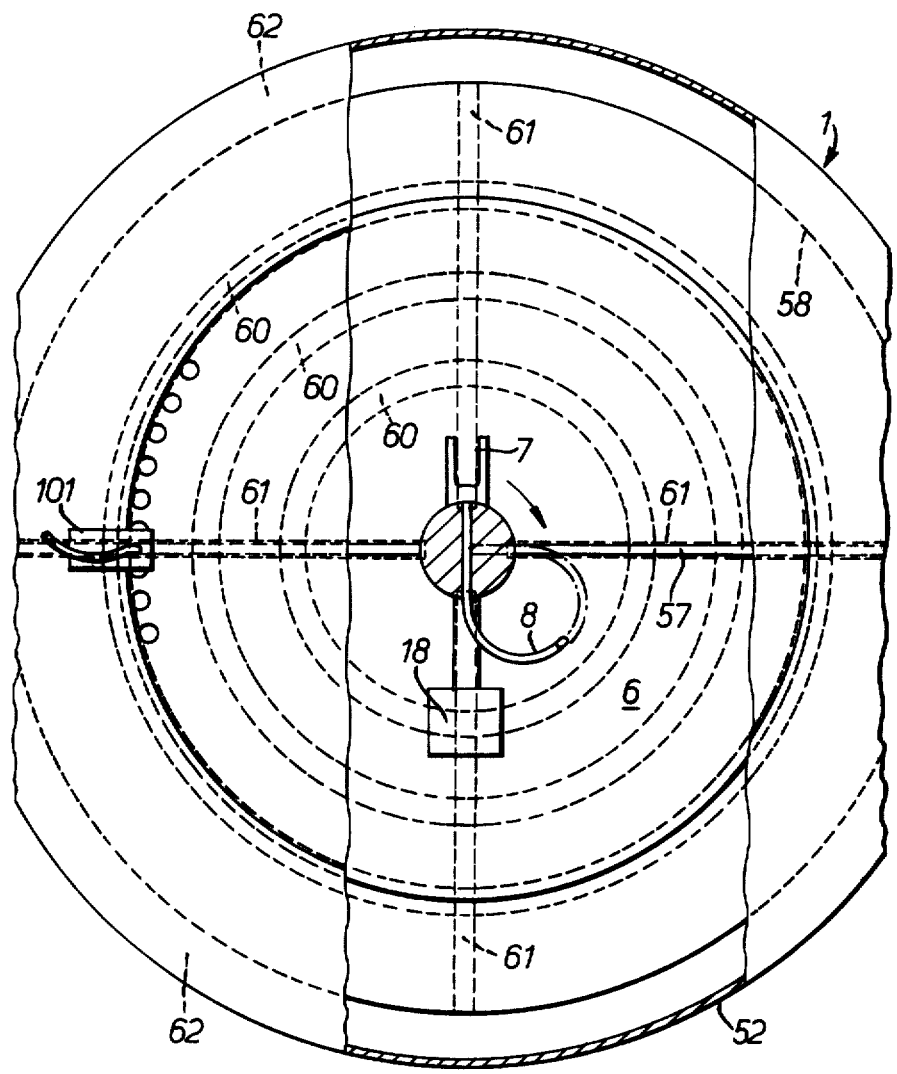

United States Patent [19]

Bunce

[11] 4,045,179

[45] Aug. 30, 1977

[54] TEMPERATURE CONTROL APPARATUS FOR USE IN INVESTIGATING SPECIMENS

[75] Inventor: Roger Abraham Bunce, Birmingham, England

[73] Assignee: Secretary of State for Social Services, London, England

[21] Appl. No.: 695,032

[22] Filed: June 11, 1976

[30] Foreign Application Priority Data

June 11, 1975 United Kingdom ............... 35118/75

[51] Int. Cl.² ......................... F27D 11/00; B01L 7/02; B01L 9/06; G01N 1/10
[52] U.S. Cl. .......................................... 23/259; 23/292; 219/413; 219/428; 219/530; 236/3; 237/3
[58] Field of Search ............... 23/259, 253 R, 292; 219/428, 413, 530; 236/3; 237/3

[56] References Cited

U.S. PATENT DOCUMENTS

| | | | |
|---|---|---|---|
| 3,057,603 | 10/1962 | Isreeli | 23/292 X |
| 3,511,613 | 5/1970 | Jones | 23/259 |
| 3,549,330 | 12/1970 | Jungner et al. | 23/259 |
| 3,634,651 | 1/1972 | Siegel | 23/259 X |

*Primary Examiner*—R.E. Serwin
*Attorney, Agent, or Firm*—Reed, Smith, Shaw & McClay

[57] ABSTRACT

The apparatus comprises a turntable carrying, in a circular array centered on a central rotational axis of the turntable, a plurality of vials extending below the underside of the turntable. A stepper motor imparts stepwise rotational motion to the turntable so that during dwell periods of the turntable, specimens in the vials can be investigated optically.

Air in a space below the turntable and bounded laterally and at the bottom by an enclosure is circulated by a rotating vane, and a thermistor, responsive to the temperature in the region of the vials, controls a heater in the space below the turntable so as to maintain the temperature of the vials at a predetermined value.

6 Claims, 3 Drawing Figures

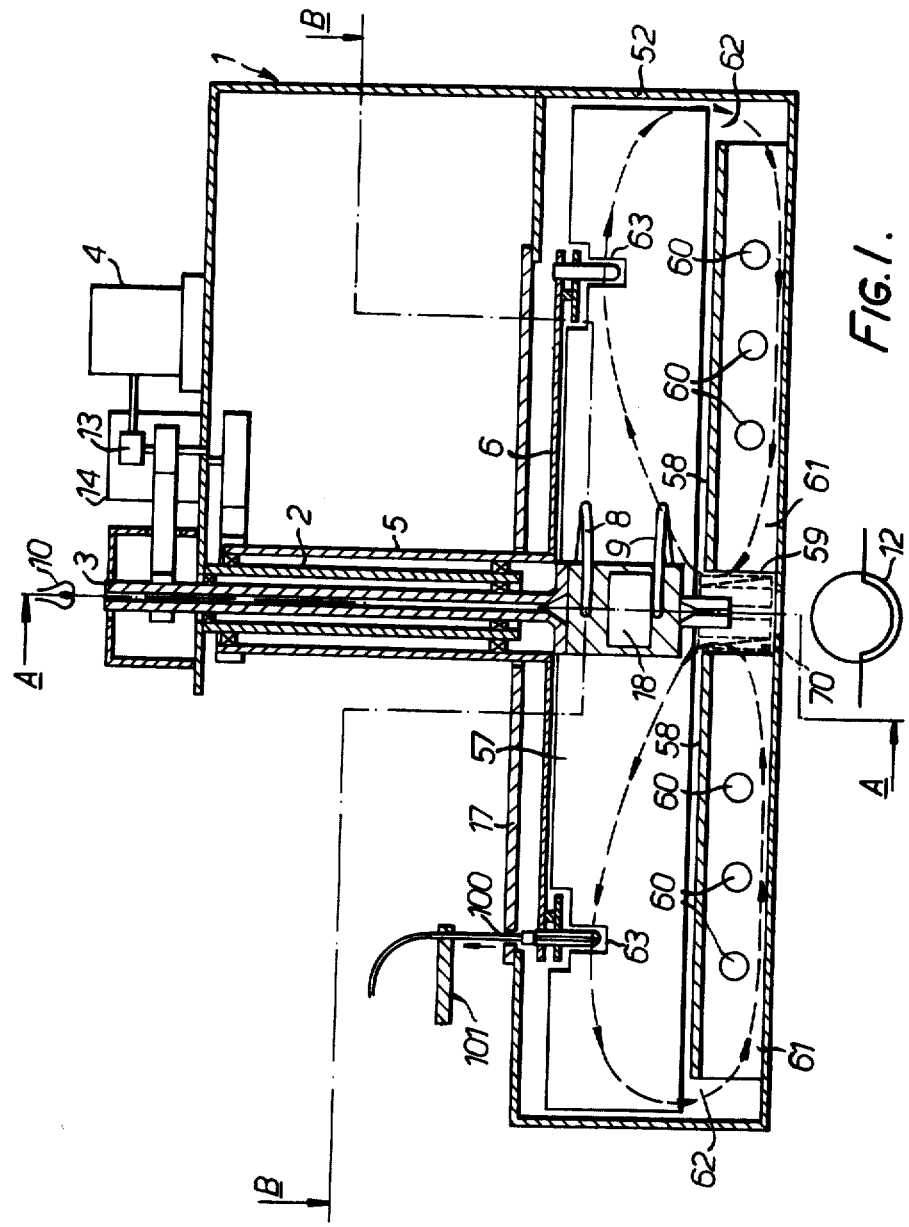
FIG. I.

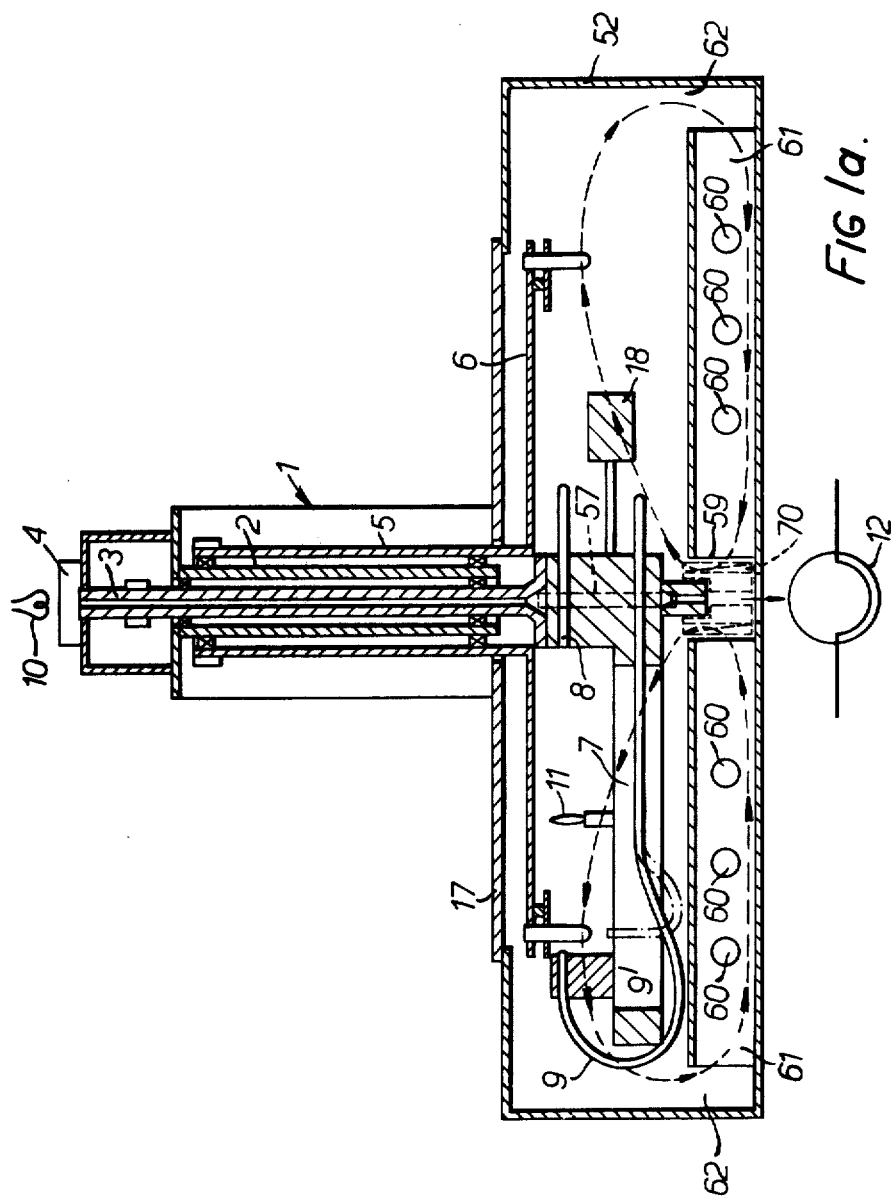

TEMPERATURE CONTROL APPARATUS FOR USE IN INVESTIGATING SPECIMENS

This invention relates to apparatus for use in investigating specimens. Specifically, the invention relates to such apparatus comprising a substantially horizontal turntable having a central rotational axis and being adapted to support, in a circular array centred on the said rotational axis, a plurality of vessels, each for containing a specimen to be investigated, the apparatus further comprising means for advancing the turntable stepwise about the said rotational axis so that, during dwell periods of the turntable, specimens may be investigated, the turntable being adapted to support the vessels in such manner that they extend downwardly below the underside of the turntable. Hereinafter, such apparatus will be termed "apparatus as specified".

In British Patent Application No. 51988/73, its divisional Application No. 46608/74, and Application No. 20389/74, there is disclosed apparatus as specified in which, in operation, the turntable is rotated stepwise by a motor relative to stationary dispensing means so that a sample of blood and a quantity of reagent (and possibly also diluent and/or dye) are provided by the dispensing means in a different, at least partially light-transmitting, vessel (taking the form of a vial) during each dwell period of the turntable between successive stepwise rotational advancements of the same. At the same time, a radially outwardly directed light beam is caused to rotate about the axis of the turntable and thereby scan the various vials in succession, and light leaving the liquid in the vials, which light is either directly transmitted light or scattered light, is received and passed to a light detector which provides an output voltage, the magnitude of which depends upon the intensity of light leaving each of the various vials and which may be used for analysis purposes of the blood samples.

In order to achieve high accuracy of analysis, it is necessary to ensure that the temperature of the vessels is maintained at a predetemined value to within close limits. It is an aim of this invention to provide apparatus with which this requirement may be achieved and which, moreover, is not confined to use in the apparatus disclosed in British Patent Applications Nos. 51988/73, 20389/74 and 46608/74 but which finds application to apparatus as specified in general.

According to the invention there is provided apparatus as specified, wherein there is a space bounded, laterally and at the bottom, by an enclosure and limited upwardly by the turntable so that when the vessels are in position, supported by the turntable, they extend into the said space, and wherein there are means provided for changing the temperature of air in said space and means positioned within said space and arranged to circulate air between the temperature changing means and the vessels wholly within said space, the temperature changing means being provided with a control device for maintaining the temperature of the said vessels substantially at a predetermined value.

Generally, the temperature changing means will be an air heater provided with control means arranged to control operation of the heater. However, should the predetermined temperature be required to be below ambient, the air heater needs to be replaced by a refrigerating device. Where the ambient temperature is expected to fluctuate above and below the predetermined temperature, the temperature changing means comprises an air heater, a refrigerating device and control means arranged to control operation of the heater and refrigerating device selectively, so as to heat or cool air in the said space.

For a better understanding of the invention, and to show how the same may be carried into effect, reference will now be made, by way of example, to the accompanying drawings, in which:

FIG. 1 shows a vertical sectional view of one form of apparatus in accordance with the invention, the apparatus being in the form of an automatic blood analysing machine, FIG. 1a is a sectional view of the machine taken along the line A—A of FIG. 1, and FIG. 1b shows a horizontal sectional view of the machine taken on the line B—B of FIG. 1 with a cover of the machine removed.

The machine illustrated in FIGS. 1, 1a and 1b is used for colorimetric, light scattering and fluorimetric evaluation of reactions between samples of blood and reagent(s), and comprises a stationary frame 1 which carries a hollow vertical trunnion 2. Extending coaxially inside the trunnion 2 is a hollow rotatable shaft 3 which is connected at its upper end by a pulley and belt arrangement and a gearbox 13 to an electric motor 4 mounted on the frame 1. The trunnion 2 is surrounded coaxially by a further rotatable shaft 5 which carries a horizontal turntable 6 at its lower end and is connected at its upper end by a further pulley and belt arrangement to a second electric motor 14, which is a stepping motor.

The turntable 6, which is covered by a stationary cover 17, is circular, its centre being on the common axis of the trunnion 2 and the shafts 3 and 5, and has about its periphery a plurality of equally spaced vials. These vials are removably fitted into notches in the turntable.

The lower part of the frame 1 is in the form of a cylindrical enclosure 52 having an inwardly projecting annular flange on the radially innermost portion of which the cover 7 is positioned. Each vial extends downwardly from the level of the turntable into the space bounded laterally and at the bottom by the enclosure and limited upwardly by the turntable 6. As can be seen in FIGS. 1 and 1a, the diameter of the turntable is slightly greater than the diameter of the opening in the top of the enclosure 52 and the turntable is arranged within the enclosure at a very small spacing below the flange of the enclosure. In this way, the transport of air between the exterior of the enclosure and its interior and vice versa is minimal.

The shaft 3 is connected at its lower end, which is below the table 6, to a horizontal arm 7 which extends radially with respect to the shaft 3. The shaft 3 is also connected to a counterbalance 18 for the arm 7. The arm 7 carries two fibre optic light guides 8 and 9. The light guide 8 has an input end at the upper end of the shaft 3 and extends vertically downwards coaxially within the shaft 3. At the lower end of the shaft 3 the guide 8 extends therefrom radially outwardly along the arm 7 and has an output end at a position along the arm which is inward of the periphery of the table 6. The output end of the guide 8 defines a slit-form output aperture. The guide 9 has an input end which is mounted on the arm 7 outward of the periphery of the table and aligned with the end of the guide 8. The input end of the guide 9 defines a slit-form input aperture. The guide 9 extends from the periphery of the table radially inwards along the arm 7 and has an output end which is directed vertically downwards along the axis of the shaft 3. FIG. 1b shows how the light guide 8 is looped between its radial and axial portions in order to avoid imposing excessive curvature on the guide. The arrangement of the guide 9 (not shown in FIG. 1b) is the same.

Above the upper end of the shaft 3 is a lamp 10 arranged to direct light vertically downwards into a circular input aperture defined by the input end of the light guide 8. Between the lamp 10 and the input aperture may be mounted a filter or grating unit for selecting the wavelength of light entering the input aperture and thereby enabling different reactions to be evaluated. Radially outwardly of the output end of the guide 8 is an optical system comprising a correction slit (not shown), converging lens 11 and a further correction slit (not shown), for focusing light delivered by the guide 8 on liquid in a vial. The optical system is clamped to a horizontal slideway, formed in the arm 7, to facilitate adjustment. Light which is transmitted by the liquid is received by the guide 9 at its input end and is delivered to its output end from which it is directed vertically downwards, along the axis of the shaft 3, to a photomultiplier 12.

The shaft 3 is also connected at its lower end to a vane 57 arranged within the space bounded by the enclosure and turntable and spaced angularly from the arm 7, about the vertical axis of rotation of the shaft 3, by 90°. The vane consists essentially of two rectangular plates which are arranged so that the longer and shorter edges of the rectangular faces of the plates are respectively radially and axially disposed relative to the shaft 3. The vane is formed with cut-out portions 63 which are slightly larger than, but conform approximately to the shape of, the vials. This enables the vane 57 to be rotated with its upper edge close to the underside of the turntable while at the same time ensuring that rotation of the vane is not impeded by the vials. In addition, the overall length end-to-end of the vane is only slightly less than the internal diameter of the peripheral wall of the enclosure.

Arranged beneath the vane on radial supporting plates 61 and with a small spacing from the vane is a horizontal annular plate 58 whose central opening 59 is coaxial with the shafts 5 and 6 and whose greater diameter is less than the length of the vane 4 from end-to-end in order to leave an annular air gap 62 between the outer edge of the annular plate 58 and the peripheral wall of the enclosure. Electric heaters 60, arranged in the form of concentric rings, are positioned in the space between the base of the enclosure and the plate 8 and extend through openings in the supporting plates 61. A thermistor (not shown), positioned within the enclosure close to the vials and responsive to the temperature within the space limited by the plate 58, turntable 6 and peripheral wall of the enclosure, is arranged to control the power supplied to the heaters 10 and thereby regulate the quantity of heat generated by the heaters so as to maintain the temperature within the space, and thereby that of the vials, at a predetermined value.

Dispensing means are provided on the flange of the enclosure 52 adjacent the periphery of the turntable 6 whereby, at a first station, a predetermined quantity of blood, together with a predetermined quantity of diluent, is dispensed into a vial when the turntable is at rest between stepwise rotational advancements and, at a second station, when the turntable is again at rest, predetermined quantities of reagent and diluent are dispensed into a vial containing blood and diluent from the first station. For this purpose a dispenser 100 is provided at each station. The dispenser is mounted on a support member 101 and is vertically displaceable to allow itself to be raised clear of the vial so that the turntable can undergo its stepwise rotational advancement. The support member 101 can be swung to one side to guide the probe over a container of blood or reagent. The dispenser is lowered into the container and a measured quantity of blood or reagent is drawn in. When the turntable next comes to rest, the dispenser is returned to its lowered position in another vial and the measured quantity is dispensed, followed by a measured quantity of diluent, into the vial.

When the blood analysing machine is in operation, the turntable 6 is rotated stepwise by the motor 14 past the dispensing means, whereat a sample of blood and a quantity of reagent (and possibly also diluent and/or dye) is placed in a different vial, as has just been explained, during each dwell period of the turntable 6 between successive stepwise rotational advancements of the table. At the same time, the motor 14 is caused to rotate the shaft 3 through at least one revolution during each dwell period, thus causing the arm 7 to rotate so that the light beam from the light guide 8 scans the vials in succession and the light transmitted by the liquids in the vials is received by the light guide 9 and passed to the photomultiplier 12 which provides an output voltage, the magnitude of which depends upon the intensity of light received by the guide 9. At the same time as the vials are scanned in succession, the vane 57 rotates with the arm 7 and in doing so it sweeps out the space limited by the plate 58, the turntable 6 and the peripheral wall of the enclosure and causes the air in this space to rotate. Owing to centrifugal force, the air passes around the individual vials in the radially outward direction, downwardly through the annular air gap 62 between the plate 58 and peripheral wall of the enclosure, radially inwardly to pass around the electrical heaters 10, and then upwardly and radially outwardly again. At the same time, the air circulates about the vertical axis of the vane 57. Thus, a circulating air pattern is set up as indicated in FIGS. 1 and 1a. The thermistor ensures that the vials, and thus the specimens, are maintained at a predetermined temperature to within close limits.

The air flow pattern achieved within the enclosure is very effective in reducing temperature fluctuations in the region of the vials projecting downwardly into the enclosure. In fact, following investigation, it has not been possible to measure any such temperature fluctuations but a maximum value of ± 0.05° C has been estimated. In a typical form of blood analysing machine, the thermal time constant of the machine is about 30 seconds and the maximum imput power consumed is about 200 watts.

The photomultiplier 12 is connected to a computer (not shown) which stores a set of data for each revolution of the shaft 3, representing the output voltage of the photomultiplier 12 for each of the vials. When the shaft 3 is rotated at least twice during each dwell period, the computer uses the several sets of data to form a mean value for the output voltage of the photomultiplier in respect of each vial. In practice, it is more convenient to rotate the motor 4 continuously rather than for it to rotate only during each dwell period of the turntable 6. Then, the computer is arranged so as to disregard the data received during each stepwise rotational advancement of the turntable 6 between successive dwell periods. Furthermore, the computer 4 is so arranged that if during each dwell period the shaft 3 rotates through a non-integral number of revolutions the computer accepts data only for the nearest integral number of revolutions of the shaft, below the actual number of revolutions undergone.

In the circumstances, therefore, the illustrated machine is used for colorimetric analysis of the blood samples. By making a slight modification, however, the machine may be used for light scattering or fluorimetric analysis of the blood samples. The modification is shown in broken lines in FIG. 1 and entails replacing the light guide 9 by a guide 9' whose input end is vertically below the vial and perpendicular to the output end of the guide 8 and placing a colour filter between the output end of the light guide 9' and the photomultiplier 12. Then the output voltage of the photomultiplier depends upon the intensity with which light from the guide 8 in a selected wavelength band, predetermined by the filter, leaves the vial.

Thus, with the blood analysing machine described, the vials are maintained at a closely controlled temperature. Thus, the reactions which take place between the blood and reagent occur under precisely controlled temperatures, so that the data obtained from the blood analysing machine assist, in highly accurate analysis of the blood samples.

With reference to FIGS. 1 and 1a, in a modification, a fan 70 is mounted centrally within the enclosure to extend from the lower edge of the vane 57 to the bottom of the enclosure. This fan is driven independently of the rotating arm 7 and vane 57. The purpose of the fan is to ensure some circulation of air within the enclosure even when the arm 7 and vane 57 are at rest, so as to avoid the possibility of the heaters 60 overheating owing to the thermistor controlling them being situated close to the vials.

I claim:

1. Apparatus for use in investigating specimens, comprising:
   a. a substantially horizontal turntable having a central rotational axis and being adapted to support in a circular array centered on the said rotational axis a plurality of specimen vessels, each such vessel being positionable to extend down below the underside of the turntable;
   b. means for stepwise advancing the turntable about the said rotational axis so that, during dwell periods of the turntable, specimens deposited during previous dwell periods in the vessels may be investigated;
   c. an enclosure disposed beneath the turntable having an internal surface symetrically positioned about the said rotational axis so as to define a space bounded laterally and at the bottom by the said enclosure and upwardly by the turntable;
   d. a baffle plate disposed within the enclosure so as to provide between this plate and the turntable a first space into which the vessels extend when supported by the turntable, and between said plate and the base of the said enclosure a second space, the outer edge of the baffle plate being separated by an air gap from the peripheral wall of said enclosure, said baffle plate being a central hole for air to circulate between said first and second spaces by way of the air gap and the said central hole;
   e. a rotary vane disposed in the said first space and mounted with its axis of rotation coincident with that of the turntable, the vane being formed with at least one cut-out portion as necessary to permit relative rotational movement between the turntable containing vessels and the vane, the shape of said vane conforming substantially the vertical cross-sectional shape of said first space so that upon rotation it sweeps out a volume substantially equal to that of the said first space:
   f. air temperature changing means disposed in said second space; and
   g. a control device for the air temperature changing means to maintain the temperature of the vessels substantially at a predetermined value.

2. Apparatus according to claim 1, wherein said temperature changing means comprises an air heater.

3. Apparatus according to claim 1, wherein said temperature changing means comprises a refrigerating device.

4. Apparatus according to claim 1, wherein said temperature changing means includes an air heater and a refrigerating device, the control device being arranged to control operation of the heater and refrigerating device selectively, so as to heat or cool air in said space bounded by the said enclosure and the turntable.

5. Apparatus according to claim 1, wherein said control device comprises a thermistor mounted to be responsive to the temperature in the region of the vessels.

6. Apparatus according to claim 2, wherein there is provided in the said enclosure fan means arranged to be driven independently of the vane being rotated, so as, even when the vane is at rest, to maintain sufficient circulation of air within said space bounded by the said enclosure and the turntable to prevent the air heater overheating.

* * * * *